United States Patent
Ben-Nun

(10) Patent No.: US 8,235,978 B2
(45) Date of Patent: *Aug. 7, 2012

(54) THERMAL CAPSULOTOMY TOOL AND SYSTEM

(75) Inventor: Joshua Ben-Nun, Moshav Beit Herut (IL)

(73) Assignee: Valens Associated Inc., Urbanizacion Obarrio (PA)

( * ) Notice: Subject to any disclaimer, the term of this patent is extended or adjusted under 35 U.S.C. 154(b) by 1177 days.

This patent is subject to a terminal disclaimer.

(21) Appl. No.: 12/013,488

(22) Filed: Jan. 14, 2008

(65) Prior Publication Data

US 2009/0216225 A1    Aug. 27, 2009

Related U.S. Application Data

(63) Continuation-in-part of application No. 11/911,111, filed on Mar. 11, 2009.

(51) Int. Cl.
*A61B 18/08* (2006.01)
(52) U.S. Cl. ............................................. 606/29; 606/34
(58) Field of Classification Search ............... 606/27–31
See application file for complete search history.

(56) References Cited

U.S. PATENT DOCUMENTS

| | | | |
|---|---|---|---|
| 4,388,990 A * | 6/1983 | Michalik | 198/867.15 |
| 4,766,897 A | 8/1988 | Smirmaul | |
| 5,269,787 A | 12/1993 | Cozean, Jr. et al. | |
| 5,873,883 A | 2/1999 | Cozean, Jr. et al. | |
| 6,066,138 A | 5/2000 | Sheffer et al. | |
| 7,125,424 B2 * | 10/2006 | Banick et al. | 623/17.11 |
| 2003/0135167 A1 * | 7/2003 | Gonnelli | 604/272 |
| 2006/0249204 A1 * | 11/2006 | Bolt et al. | 137/68.14 |
| 2007/0220812 A1 * | 9/2007 | Valentage et al. | 49/502 |

FOREIGN PATENT DOCUMENTS

WO    WO 2006/109290    10/2006
WO    PCT/IL2005/000461    11/2006

* cited by examiner

*Primary Examiner* — Michael Peffley
*Assistant Examiner* — Daniel Fowler
(74) *Attorney, Agent, or Firm* — Law Offices of Edward Langer Adv. and Patent Attorney

(57) ABSTRACT

A system and tool for performing a capsulotomy procedure. The system includes an air pressure unit, a capsulotomy and movement control unit providing electrical current and movement control, and a capsulotomy tool, and an extendable-retractable burning element coupled to the tool. A capsulotomy and movement control unit provides electrical current to the burning element and movement control for extending and retracting the burning element. When the burning element is in a flattened, retracted configuration, the tip of the tool can be inserted through a relatively small corneal incision. Then, the burning element is opened to a circular, extended configuration, allowing a capsulotomy by applying an electrical pulse to the burning element. Optionally, predefined points of weakness allow removal of the tool should breakage occur during surgery.

20 Claims, 16 Drawing Sheets

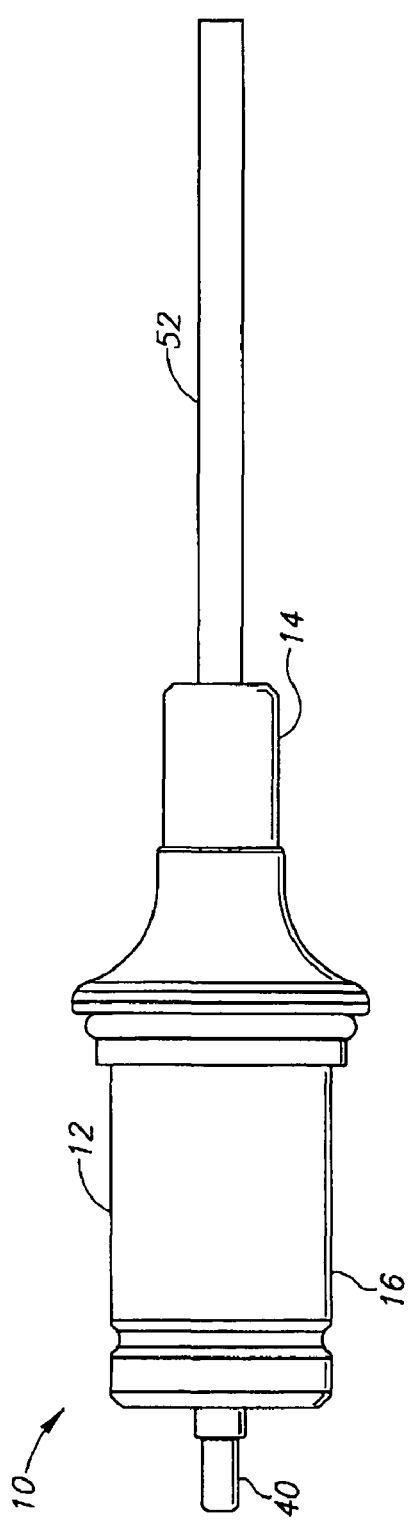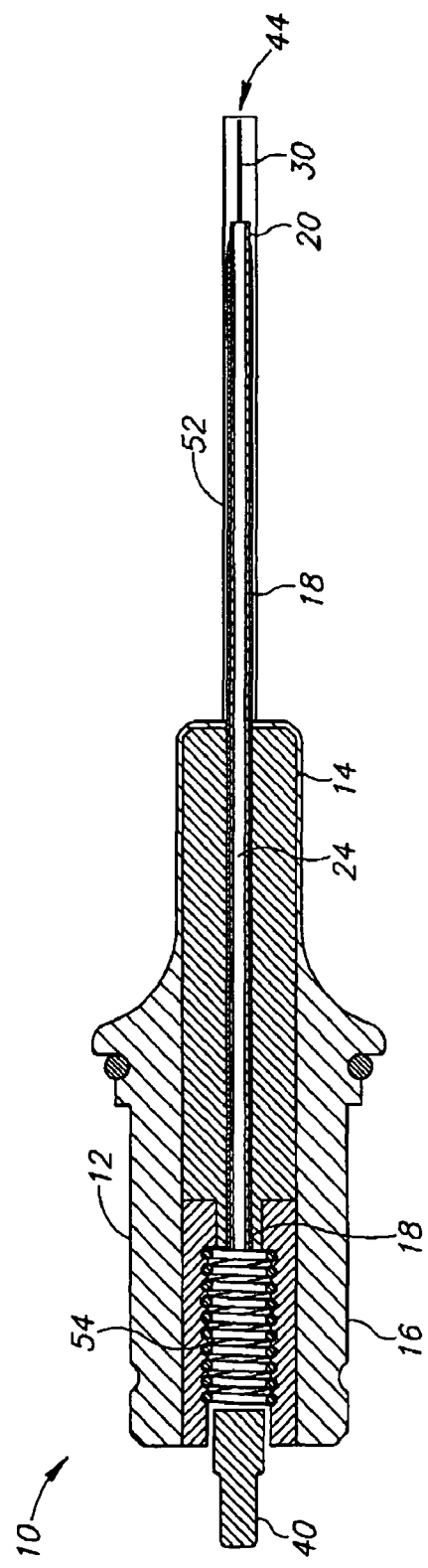

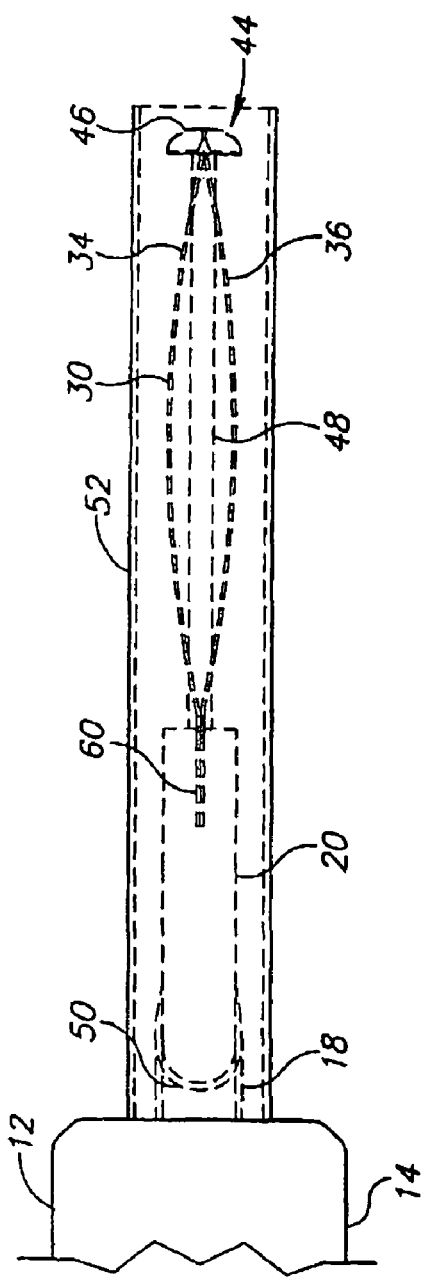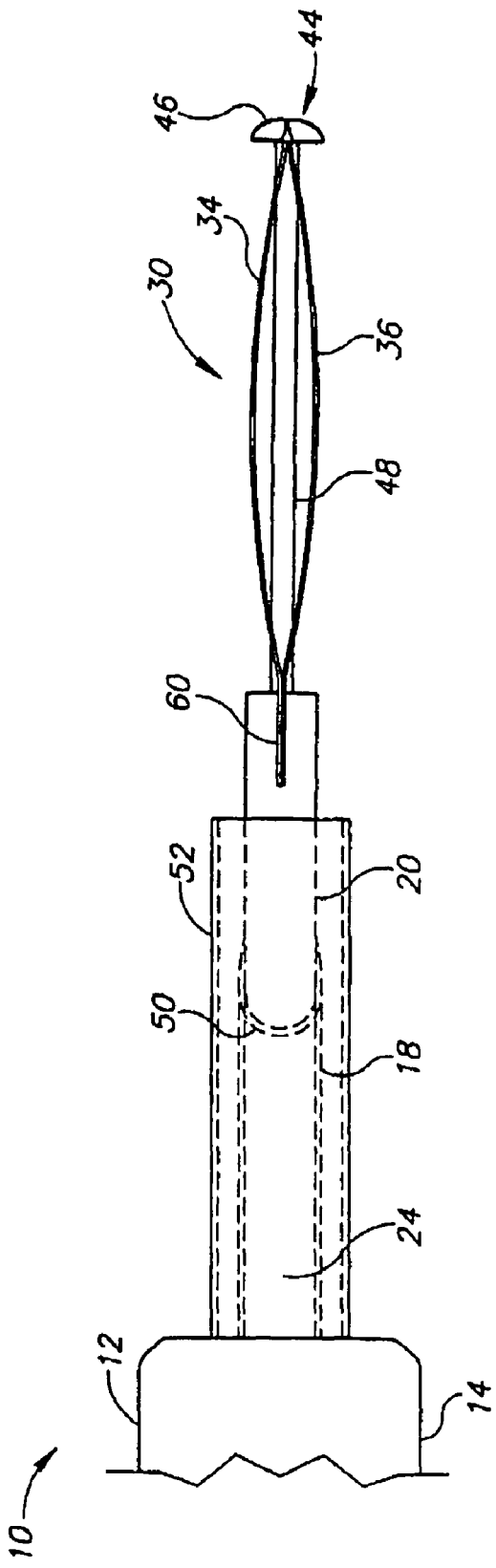
FIG.3A
FIG.3B

THERMAL CAPSULOTOMY TOOL AND SYSTEM

CROSS-REFERENCE TO RELATED APPLICATIONS

The present application is a Continuation-in-Part of U.S. patent application Ser. No. 11/911,111 filed Mar. 11, 2009 by the Applicant.

FIELD OF THE INVENTION

The present invention relates to a field of cataract surgery. More specifically, the present invention relates to a system and tool for performing a capsulotomy procedure.

BACKGROUND OF THE INVENTION

To date, over one million cataract surgeries are performed annually in the United States, in which the anterior lens capsule must be opened to gain access to the lens nucleus and allow removal of degenerated cortical material. It is necessary to create a relatively large circular opening in the lens capsule in order to enter the lens interior and to withdraw matter from inside. Formation of this opening is known as a capsulotomy. It is important that the opening has smooth edges and is tear resistant so that the lens contents can be easily removed through the opening. The lens opening is usually on the order of 5-7 millimeters in diameter, though this may vary.

Currently, two techniques for anterior capsulotomy are widely used: the "can-opener" technique and capsulorrhexis. In can-opener capsulotomy, a small incision in the sclera or peripheral cornea is performed, then a cystotome, knife, or needle is inserted through the incision and small connecting tears are made in the anterior lens capsule in a circular pattern. After a complete circle has been made by connecting the tears, a circular piece of the anterior capsule is grasped with forceps and torn away along the perforations. Unfortunately, when opening the capsule with numerous small capsular tears, the small tags that remain become a focal area of least resistance and can lead to tears, which extend radially and posteriorly to the posterior capsule. The detrimental result is a loss of structural stability of the capsule and an increased likelihood of vitreous entry into the anterior chamber.

Capsulorrhexis denotes a circular central opening in the anterior capsule. This continuous opening eliminates the residual tags common with the can-opener technique described above. In capsulorrhexis, a capsular incision is made with a cystotome, and this incision is coaxed to form a circular shape by pushing the leading edge of the freshly tearing capsule with the cystotome in a non-cutting fashion or by grasping the leading edge with forceps. This procedure is challenging for the surgeon to control. The tearing motion can lead to an undesirable tear toward the equator and the posterior capsule, and the size of the opening is difficult to dictate. Capsulorrhexis requires a significant amount of skill and experience and to consistently obtain successful results.

Opening the anterior capsule via either of the described techniques of anterior capsulotomy is a delicate procedure and is widely considered to be one of the most difficult steps in cataract surgery. A poorly performed anterior capsulotomy significantly hinders the subsequent surgical steps and increases the probability of operative complications. Complications resulting from a poor capsulotomy include zonular stress with subsequent breakage of the posterior capsule, vitreous loss, and large capsular tags preventing efficient lens removal. A poor capsulotomy also prevents placement of an intraocular lens in the capsular bag due to ill-defined capsular structures. The operative time is lengthened and patient discomfort can be increased, along with the risk of postoperative complications and decreased visual acuity results.

With either of the above-described techniques for anterior capsulotomy, the size or position of the capsular opening is often not ideal. The location, size, and configuration of the incision have important consequences. For example, an overly small capsular opening can impair the safe removal of the lens nucleus and cortex and prevent proper intraocular lens insertion into the lens capsule. In addition, a small or eccentric capsular opening places excessive stress on the lens capsule during surgery, placing the eye at risk for zonular and capsular breakage.

Certain devices have been proposed to overcome the problems associated with conventional anterior capsulotomy techniques. For example, U.S. Pat. No. 4,766,897 issued to Smirmaul, and U.S. Pat. Nos. 5,269,787 and 5,873,883 issued to Cozean Jr. et al. each disclose instruments that include circular cutting members for incising the anterior capsule. However, use of such devices in small incision cataract surgery is limited due to their size. Specifically, the anterior lens capsule of the eye is shielded by the cornea and sclera, such that a passage wound must be cut in the corneal or scleral tissue before any surgical apparatus can reach the anterior capsule. It is desirable to limit the width of the passage wound incised on the corneal tissue, preferably to 1-3 millimeters. A small wound decreases the scope of the surgical closing procedures, promotes rapid healing, minimizes astigmatism, reduces potential infections, and offers rapid visual rehabilitation. Therefore, the instrumentation employed in cataract surgery should be capable of passing through a small wound. Prior art cutting members cannot be passed through a small corneal incision of 1-3 mm.

Burning tools exist in which heat is concentrated at the tip, and the tip is made to contact and burn a surgical site. In use of such burning tools for cataract surgery, an incision is made in the cornea, and the tip of tool is inserted through the incision and brought into contact with the capsule, where it is activated to sear through the capsule. The use of prior art burning tools is restricted by the small size of the incision, as previously mentioned, which hampers introduction of a large tip having a circular shape of the appropriate size of the desired seared area.

International application PCT/IL05/000461 by the Applicants describes a burning ring present at an oblique angle on the end of a narrow-diameter shaft. The burning ring can therefore be introduced through a small incision, and the oblique angle grants a relatively large elliptical burn, with the largest axis of the burn being larger than the diameter of the shaft.

U.S. Pat. No. 6,066,138 to Sheffer et al. describes a searing cautery that is retractable from within a handle, so that the cautery can be extended to its final size after insertion through the corneal incision. The Sheffer patent suffers from the disadvantage that the burning ring does not close a complete circle, as apparent in FIG. 1b, with the area near the handle not being seared. Therefore, it is still necessary to grasp that remaining area with a forceps, and form a tear that is difficult to control. Additionally, since the searing ring is formed from a single metal wire extending substantially into the depths of the handle, when the wire is heated electrically, it is difficult to insulate the tool and prevent heating in unwanted areas. Searing could accidentally occur in other portions of the eye adjacent to the lens, since the handle of the tool could heat, and since the tool needs to be inserted considerably into the eye.

Other burning tools exist which have a small diameter tip, which is inserted through the incision, and used to burn a series of holes in the capsule, arranged in a ring, which is then grasped with forceps and torn into a circular opening. It is difficult to manipulate the burning tool to form a series of burns that are reliably ring-shaped and are present at the desired location, and form a ring of the desired size. Also, in cataract surgery, the procedure is usually complicated by the need for multiple instruments: a cutting tool, an air pressure inlet, a water pressure inlet, and related surgical and electrical equipment.

My previous invention, described in International Publication No. WO 06/109290, disclosed a surgical tool which provides both regulated heating and airflow pressure directed to a surgical site. The tool is capable of passing through a relatively small corneal incision and can easily form a large diameter ring-shaped opening in the capsule.

The tool overcame the need for multiple instruments in cataract surgeries as it provides both regulated heating and airflow pressure directed to a surgical site. Furthermore, the tool is convenient to handle, can be inserted through a small diameter (1-2.8 millimeters) incision in the cornea, and is capable of reliably creating a uniform circular-shaped opening of approximately 4-7 millimeters in the lens capsule.

The surgical tool described in WO 06/109290, overcomes major problems associated with prior art tools. However, the scenario in which the tool breaks while in the eye, was not addressed in my previous patent, and since the possibility of failure during surgery always exists, the design of the tool should be such that in case of breakage, it will be possible to remove the tool immediately from the eye without damage to the eye.

The present invention enlarges on the previous concept, describing a design aspect allowing straightforward removal of the tool from the eye in case of breakage of the tool during surgery, without damage to the eye.

SUMMARY OF THE INVENTION

Accordingly, it is a principal object of the present invention to provide a thermal system and tool for the performance of a capsulotomy that effects formation of an opening in the lens capsule through the use of a short pulse of electrical current. The heat generated from the current instantaneously burns an opening of a predetermined size in the lens capsule.

Moreover, the system and tool of the present invention is adapted for maintaining a pressurized airflow to the surgical site so that additional airflow control devices are not required.

Additionally, the system and tool of the present invention has an expandable-retractable burning element that enables approaching the lens through a small corneal incision (about 1.5 millimeters) while allowing for a capsulotomy having a diameter, for example, of about 5-7 millimeters.

In accordance with a preferred embodiment of the present invention, there is provided a system for performing a capsulotomy procedure, comprising a capsulotomy tool comprising a main housing having a distal end and an extendable-retractable burning element coupled to the distal end of the main housing and a capsulotomy and movement control unit. The capsulotomy tool is in connection with the capsulotomy and movement control unit for providing electrical current and movement control to the burning element such that when the burning element is extended and heated, an opening is burned on the lens capsule.

According to a preferred embodiment of the present invention, the burning element comprises first and second electrically-conductive bands having opposite ends that are connected between the end of the inner tube and the tip of the outer tube.

In a preferred embodiment, the first and second bands each have a groove upon them, with the groove representing a predefined point of weakness. In the undesirable scenario in which the electrical current is excessively high, breakage will occur at these predefined points of weakness. Should this occur while the tool is within the eye, the location of the grooves upon the bands is such as to nevertheless allow retraction of the broken bands into the sleeve prior to the removal of the tool from the eye. The tool can be immediately removed from the eye without damaging the eye. Preferably, a single groove is present on each band, and each groove is situated near the end of its respective band, close to the tip of the outer tube. The broken bands thus remain connected at the end of the inner tube, and can be retracted and removed from the eye.

According to preferred embodiments of the present invention, the system also comprises a handle for connecting between the tool and the capsulotomy and control unit. The burning element for performance of the capsulotomy is retracted from the capsulotomy tool portion beyond the handle, and this tool portion is for disposable, one-time use.

According to further preferred embodiments of the present invention, the system also includes an air pressure unit and airflow means coupled to the air pressure unit for directing pressurized air to the surgical site.

In accordance with another preferred embodiment of the present invention, there is provided a tool for performing a capsulotomy, comprising;
(a) a main housing having a proximal end and a distal end;
(b) an extendable-retractable burning element coupled to the distal end of the main housing and adapted for being switched between a retracted configuration and an extended configuration;
(c) an airflow channel extending through the main housing and terminating proximal to the burning element;
(d) airflow means coupled to the airflow channel for supplying pressurized airflow; and
(e) capsulotomy and movement control means coupled to the main housing for providing electrical current to the burning element and movement control for controlling extending and retracting of the burning element;
wherein the burning element is insertable within the eye through a small corneal incision when the burning element is in a retracted configuration, and the burning element is adapted to perform a capsulotomy of a predetermined size when it is in an extended configuration, and when an electrical current is applied thereto.

Other features and advantages of the present invention will become more readily apparent and understood from the detailed description section that follows.

BRIEF DESCRIPTION OF THE DRAWINGS

For a better understanding of the invention with regard to the embodiments thereof, reference is made to the accompanying drawings, in which like numerals designate corresponding elements or sections throughout and in which:

FIG. 1 is a side view of a capsulotomy tool, according to a preferred embodiment of the present invention;

FIG. 2 is a cross-sectional side view of a capsulotomy tool, according to a preferred embodiment of the present invention;

FIG. 3a is a partial cross-sectional side view of the embodiment, showing the burning element of the tool in a completely retracted configuration;

FIG. 3b is a second partial cross-sectional side view, showing the burning element of the tool as it is being advanced from within the sleeve of the tool;

DETAILED DESCRIPTION OF THE PREFERRED EMBODIMENTS

Figure 4:
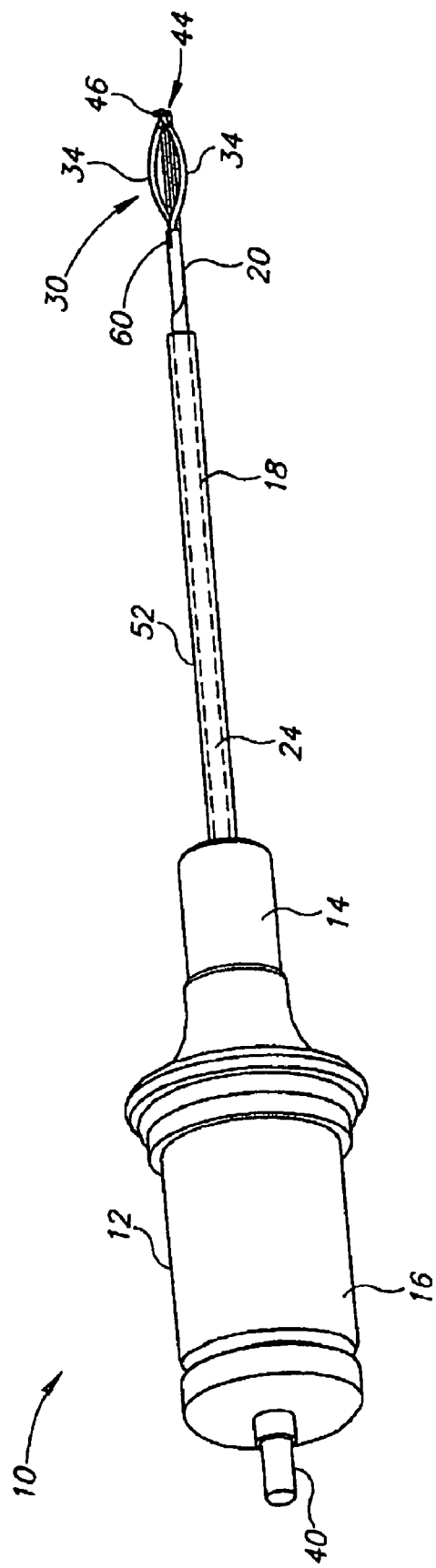
FIG. 4 is a perspective view of a capsulotomy tool, showing the burning element in an extended configuration.

The present invention discloses a capsulotomy tool, which has a retractable cautery ring, also known as a burning element. The burning element is initially hidden within a sleeve. After the tool is inserted past the capsular incision, the burning element is progressively extended from within the sleeve by sliding outwards several concentrically arranged tubes with which the element is associated. Finally, the burning element is fully opened to expand into a complete circular or complete oval shaped cautery, which is then heated to sear the lens. The complete circular or oval-shaped searing thus eliminates the need for tearing by forceps, which is potentially dangerous and difficult to perform.

In the invention, heating is limited to the burning element, so there is no danger of searing inappropriate areas of the eye. The retractable nature of the burning element allows it to be introduced through a small capsular incision, yet provides burning on the lens at a diameter larger than that of the small capsular incision. The tool additionally provides pressurized airflow through its hollow center, alleviating the need for a separate airflow tool.

FIGS. 1-6 show a preferred embodiment for a capsulotomy tool 10, constructed and operated in accordance with the principles of the present invention.

Referring to FIG. 1, capsulotomy tool 10 includes a main housing 12 having a distal end 14 and a proximal end 16. Main housing 12 includes a connector 40 at proximal end 16 for facilitating connection of main housing 12 to a handle which is operably connected to a capsulotomy and movement control unit and to an air pressure unit for providing electrical current and pressurized air, respectively, to capsulotomy tool 10. This will be described further herein with respect to FIGS. 7a-b.

Capsulotomy tool 10 includes a sleeve 52 that extends from distal end 14 of main housing 12. Initially, sleeve 52 is disposed over surgical elements of capsulotomy tool 10, to be described further herein. Sleeve 52 is formed from a non-conductive material, such as plastic or Teflon, and has smooth sides such that entry into the eye can be achieved with minimal friction. The end of sleeve 52 is tapered around the edges. This serves to ease of entry into the eye after an incision has been made. Sleeve 52 also provides a seal against the corneal incision after the eye has been entered.

Referring to FIG. 2 and best shown in FIGS. 3a-b, capsulotomy tool 10 includes an outer tube 18 having a distal end 44. End 44 comprises a tip 46 and an outer tube extension 48 having a truncated circumference that extends between the completely tubular region (region not having a truncated circumference) of outer tube 18 and tip 46. The region where outer tube 18 changes from a completely tubular construction to extension 48 has a beveled edge 50, which provides extra structural support for outer tube extension 48, so that extension 48 can be made as thin as possible. Beveled edge 50 may be beveled to any suitable angle, for providing maximal support to extension 48.

Capsulotomy tool 10 also includes an inner tube 20 that passes through the central axis of main housing 12, and that extends from distal end 14 of main housing 12 and through outer tube 18. The hollow center of inner tube 20 defines an air channel 24 (see FIG. 2) for directing pressurized airflow to the surgical site. Air channel 24 is operably coupled to the air pressure unit (described below in FIG. 7b) for receiving pressurized air. It will be appreciated that by providing airflow, the surgical site remains dry while the capsulotomy is performed. Pressurized airflow also serves to keep the anterior chamber of the eye open and expanded while the lens capsule is being opened.

Referring to FIG. 2, both inner tube 20 and outer tube 18 are coupled to a spring mechanism 54 located in main housing 12, for enabling combined movement of inner tube 20 and outer tube 18 out of sleeve 52, as well as for enabling movement of inner tube 20 within outer tube 18. This will be described further herein. It will be noted that as shown in FIG. 2, inner tube 20 is positioned inside of outer tube 18.

According to a preferred embodiment, all elements shown in FIG. 2 are disposable, and are intended for a single use. This includes housing 12, spring mechanism 54, inner tube 20, outer tube 18, sleeve 52, as well as burning element 30 (to be described herein below).

Referring to FIGS. 3a and 3b, an extendable-retractable burning element 30 is connected to the end of inner tube 20. FIG. 3a illustrates the burning element 30 in its retracted state, within the sleeve 52. FIG. 3b illustrates the burning element 30 after it has been extended out of the sleeve 52.

Figure 6:
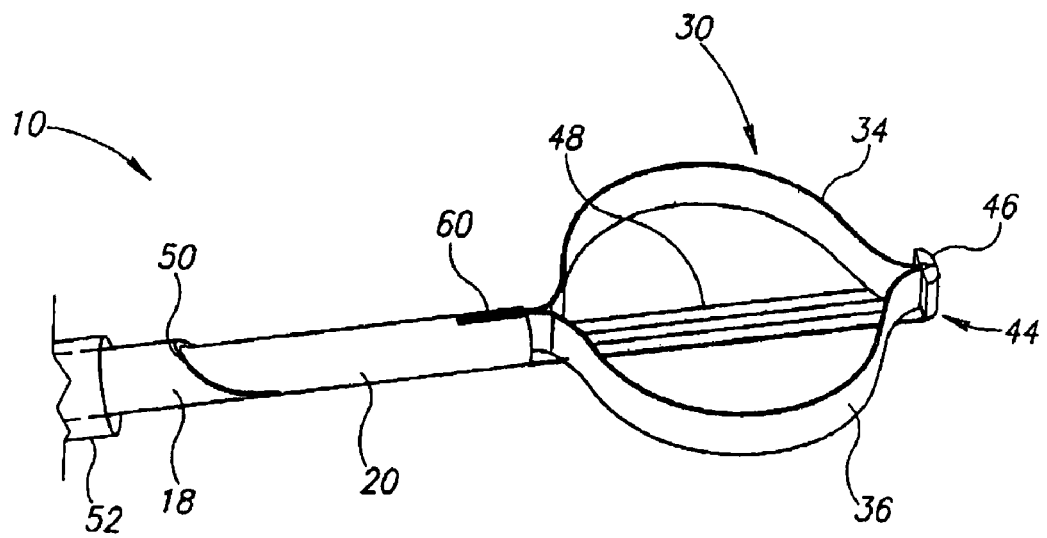
FIG. 6 is a partial view of a capsulotomy tool, showing the burning element in a completely opened configuration.

Burning element 30 includes a first band 34 and a second band 36, which are formed from electrically conductive material such as, though not limited to, a tungsten alloy. The opposite ends of each band 34, 36 are vertically connected between the end of inner tube 20 and tip 46 of outer tube 18. Movement of inner tube 20 in the direction of tip 46 of outer tube 18 causes first band 34 and second band 36 to adopt the extended and open configuration, in which bands 34, 36 substantially form a circle with one another, as shown in FIG. 6. A spring mechanism 54 is provided for enabling movement of inner tube 20 and of outer tube 18. It is appreciated that other mechanisms could be employed, as are well known in the art, for effecting outward movement of inner tube 20 and outer tube 18.

Sleeve 52 covers outer tube 18 and inner tube 20 during passage of the tip of the capsulotomy tool 10 through the corneal incision. By providing sleeve 52 as a cover for outer tube 18, as well as for inner tube 20 and burning element 30, the entry into the eye can be accomplished quickly and with minimal friction.

Referring to FIG. 3b, once the anterior chamber has been reached, outer tube 18 and inner tube 20 are advanced from the end of sleeve 52. When tip 46 is in proximity to the lens capsule, inner tube 20 is advanced so as to cause burning element 30 to be switched from the retracted configuration to the extended and opened configuration (see FIGS. 4, 5, and 6). The burning element is then positioned on the capsule. A brief pulse of electricity sent through the tool then causes bands 34, 36 of burning element to heat up and burn an opening in the lens capsule.

As mentioned previously, sleeve 52 also serves the purpose of providing a seal against the cornea once the end of capsulotomy tool 10 has been inserted into the eye. It will be noted that in FIG. 1, sleeve 52 conceals outer tube 18 and burning element 30 from view.

In the retracted configuration, bands 34, 36 of burning element 30 are positioned substantially flattened and parallel to one another, directly above extension 48 of outer tube 18. In FIGS. 1, 2, 3a and 3b, burning element 30 is in the retracted configuration (in FIG. 1, the burning element is not visible). In FIGS. 1, 2, and 3a burning element 30 is located inside of sleeve 52. In this position, the end of capsulotomy tool 10 can be inserted into a relatively small corneal incision, on the order of 1-2 millimeters.

In FIG. 3b, burning element 30 has been partially advanced out of sleeve 52, though it is still in the retracted configuration. Movement of burning element 30 out of sleeve 52 is accomplished by moving outer tube 18 and inner tube 20 such that extension 48 and burning element 30 become exposed from the end of sleeve 52 Thereafter, inner tube 20 is moved towards tip 46 of outer tube 18, while outer tube 18 remains stationary, thereby causing each of bands 34, 36 to assume an arched, semi-circular configuration.

Figure 5:
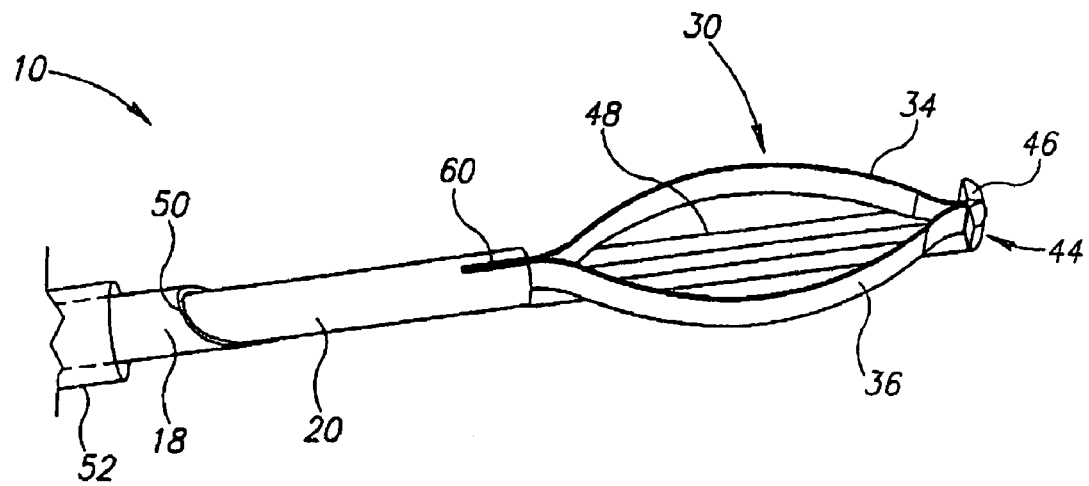
FIG. 5 is a partial view of a capsulotomy tool, showing an enlargement of the burning element in a partially opened configuration.

Referring to FIGS. 4-6, the extended and opened configuration is shown, though in FIG. 5, bands 34, 36 have been only partially opened.

The height of bands 34, 36 is about 200 microns higher than that of inner tube 20 and tip 46, so that when the edges of bands 34, 36 contact the capsule, no other elements of capsulotomy tool 10 will contact it. Inner tube 20 is provided with a slot 60 formed in the upper edge at the end thereof for accommodating the additional height of bands 34, 36.

Referring to FIGS. 5 and 6, the length of first and second bands 34, 36 is designed according to the size of the capsulotomy that is required. For example, for a capsulotomy of 4-5 millimeters, a band length of about 7 millimeters is required. The band length is approximately half the circumference of the required capsulotomy. Extension 48 of outer tube 18 must also be of sufficient length so as to accommodate bands 34, 36 when they are in the flattened, retracted configuration. The angle of beveled edge 50 can be made larger or smaller depending on the length of extension 48.

Optionally, before use the burning element 30 is removed from the tool 10, so that the size of the burning element can be selected in order to choose the size of the capsulotomy. Preferably, several removable burning elements can be designed having longer or shorter bands, in order perform a capsulotomy having a diameter selected from most preferred diameters 4, 5, 6 or 7 mm. Removable burning elements of other sizes can also be envisioned.

First and second bands 34, 36 are formed from electrically conductive material such as a tungsten alloy or any other suitable element. Inner tube 20 and outer tube 18, are both formed, at least partially, from electrically-conductive material. Extension 48 and tip 46 of outer tube 18, are likewise formed from the same material. Inner tube 20 and outer tube 18 define opposite poles of an electrical circuit, and they are designed so as to be electrically insulated from one another.

To perform a capsulotomy, a brief low-voltage electrical pulse is passed through bands 34, 36. When a current is passed through inner tube 20, bands 34, 36, tip 46, extension 48, and returning through outer tube 18, bands 34, 36 will heat up (or vice versa depending on the polarity).

It will be appreciated that a switch is provided such that the electrical circuit can be completed only when burning element 30 is in the extended configuration, so as to prevent premature heating of burning element 30.

Figure 7A:
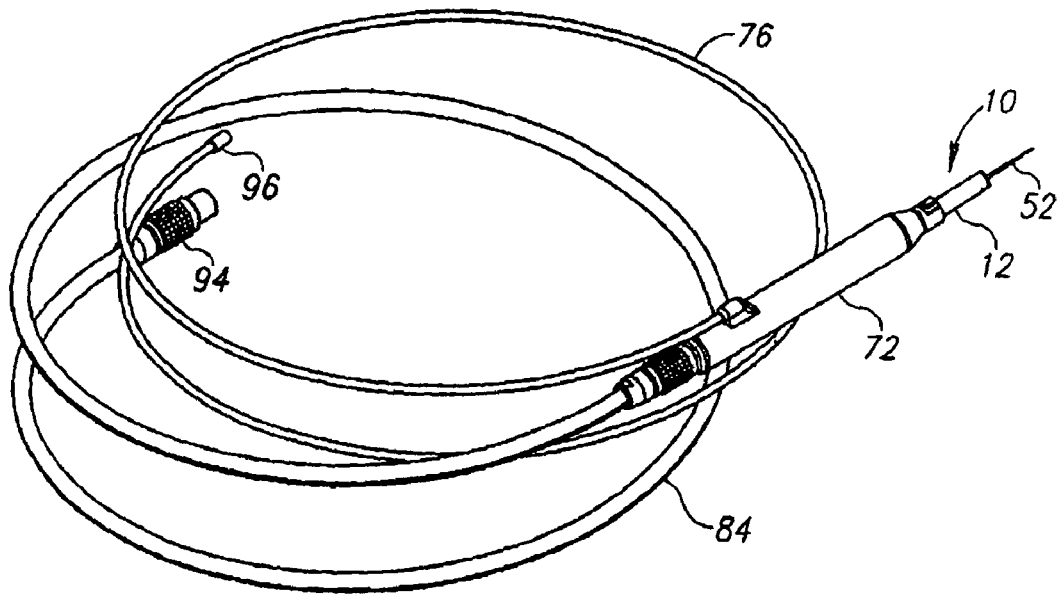
FIG. 7a is a schematic view of part of a system for the performance of a capsulotomy, according to a preferred embodiment of the present invention.
Figure 7B:
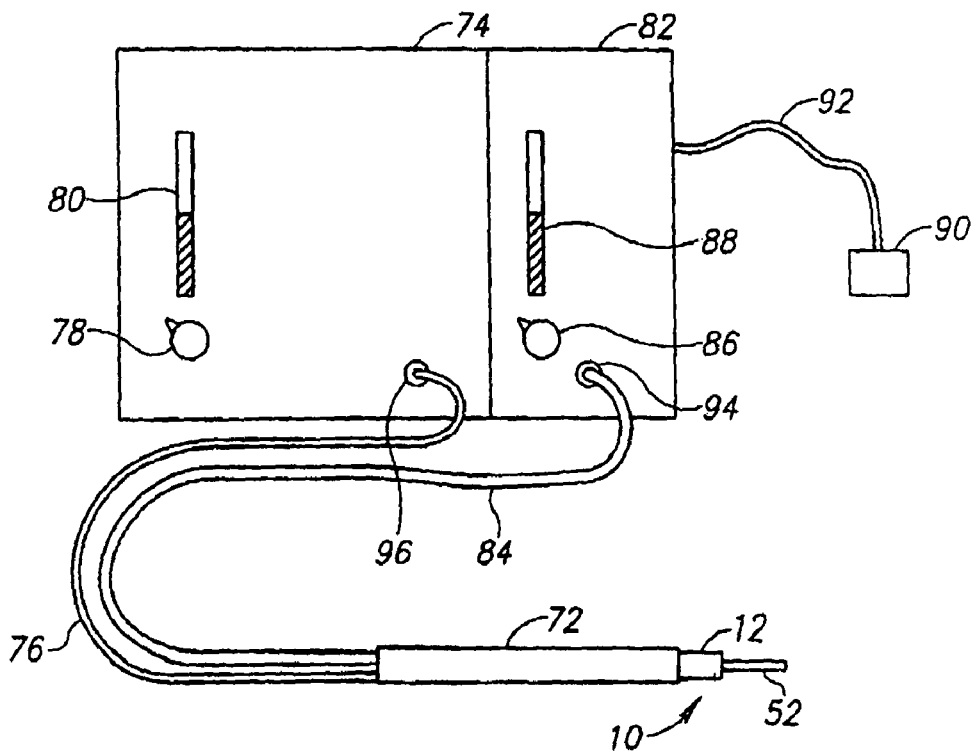
FIG. 7b is a general schematic diagrammatic view of a system for the performance of a capsulotomy, according to a preferred embodiment of the present invention.

Reference is now made to FIGS. 7a and 7b, and to a system for the performance of a capsulotomy employing the capsulotomy tool described above.

Capsulotomy tool 10 is coupled to a handle 72 which facilitates maneuvering of tool 10 by the surgeon. Handle 72 houses a motor (not shown) that is connected to spring mechanism (54, see FIG. 2) of main housing 12 for enabling reversible movement of the outer tube 18, the inner tube 20, and the extending and retracting of the burning element 30.

Handle 72 is coupled to an air pressure unit 74 via an air tube 76 having a connector 96 at the end thereof, for supplying pressurized air to the surgical site during performance of the capsulotomy. Air pressure unit 74 preferably includes a control 78 and a display 80 for determining the amount of pressurized air delivered to the air channel of capsulotomy tool 10.

Handle 72 is further coupled to a capsulotomy and movement control unit 82 via a power cable 84 having a connector 94 at the end thereof, for supplying electrical current and movement control to capsulotomy tool 10. Capsulotomy and movement control unit 82 also includes a control 86 as well as a display 88 for determining the amount of electrical current applied through power cable 84 to capsulotomy tool 10. Power cable 84 is connected to the motor inside of the handle 72 for facilitating movement of the outer tube 18 and inner tube 20 of capsulotomy tool 10.

A foot-pedal control switch 90 is also connected to capsulotomy and movement control unit 82 via a cord 92. Foot-pedal control switch 90 enables the surgeon to control the movement of the inner and outer tube 20, 18 and the extending and the retracting of the burning element 30, as well as applying of electrical current, with his foot.

Operation of capsulotomy tool 10 will now be described, when used for creation of a seared capsulotomy opening during cataract surgery.

In FIGS. 8-13, illustrations are schematic and relative sizes are not necessarily accurate. In reality, the capsulotomy opening encompasses approximately half to two thirds of the area of the lens, with the capsulotomy opening usually being within the range of 4-7 mm.

Figure 8A:
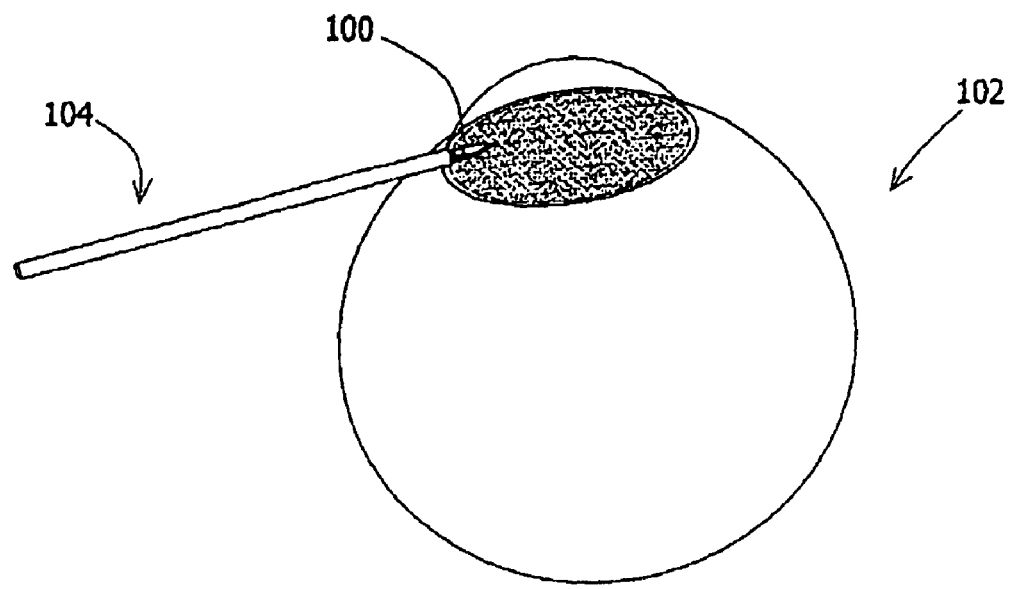
FIGS. 8a-b illustrate the procedure for creating a corneal incision as a first step in cataract surgery.
Figure 8B:
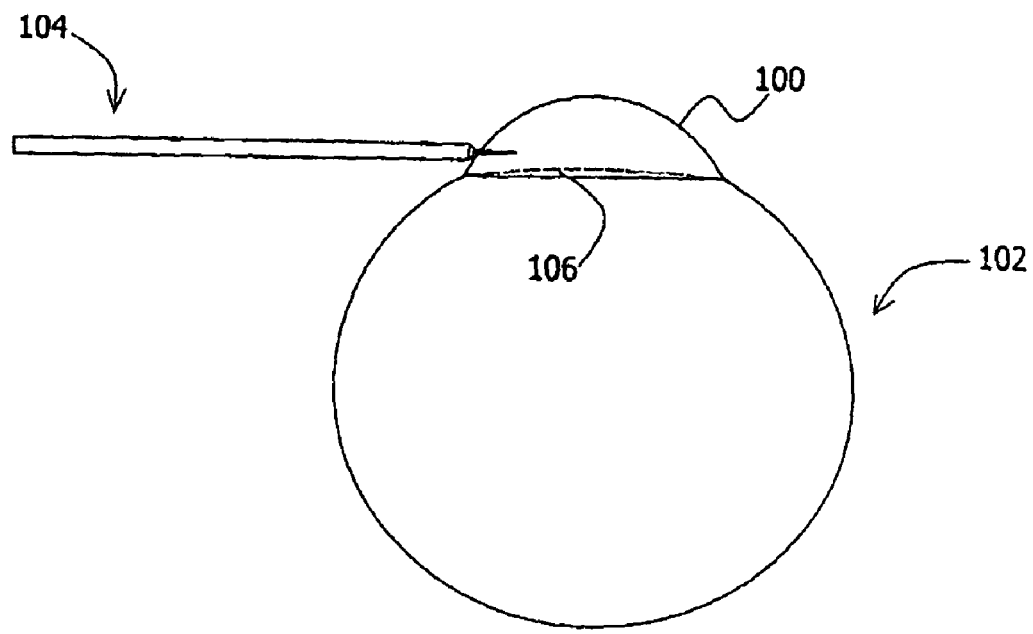

Referring to FIGS. 8a and 8b, the surgeon first makes a small incision in the cornea 100 of the eye 102, preferably on the order of 1-2 millimeters diameter, using a standard scalpel 104.

Figure 9A:
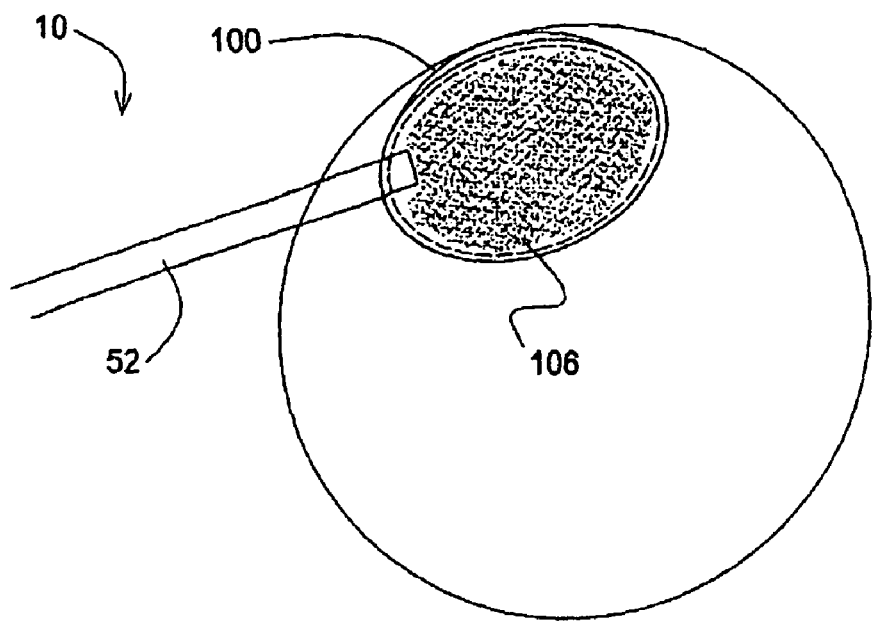
FIGS. 9a-b illustrate delivery of airflow in a second step in cataract surgery performed using the invention.
Figure 9B:
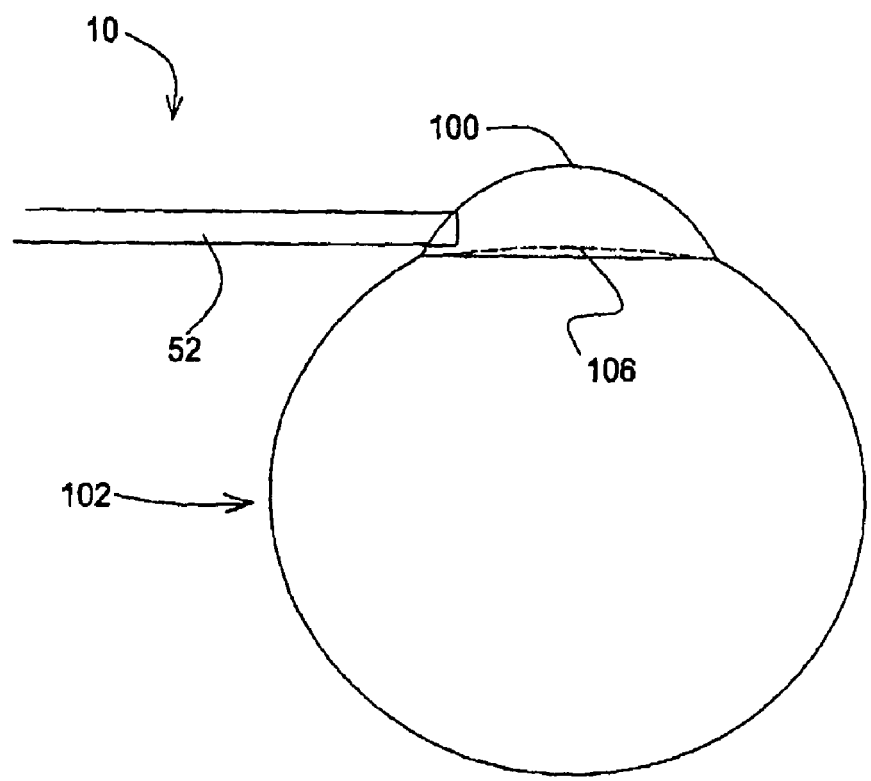

Referring to FIGS. 9a and 9b, following formation of an incision in the cornea 100, the end of capsulotomy tool 10 is inserted through the incision, with capsulotomy tool 10 in the configuration shown in FIG. 1, with inner tube 20, outer tube 18 and burning element 30 disposed inside of sleeve 52. A burst of pressurized air is delivered to the cornea 100, through air channel 24 present at the hollow center of inner tube 20 (shown in FIG. 2). The pressurized air assists in retaining the shape of the cornea 100, and moves fluids to behind the lens 106, allowing further steps of the procedure to be performed on a relatively dry lens 106.

Figure 10A:
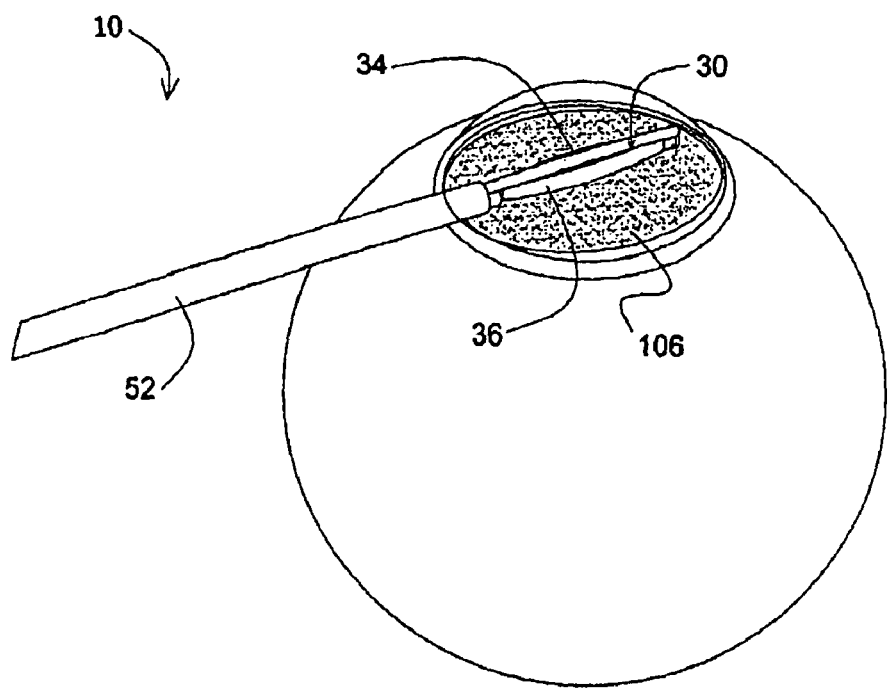
FIGS. 10a-b illustrate extension of the burning element from within the sleeve, as a third step in cataract surgery performed using the invention.
Figure 10B:
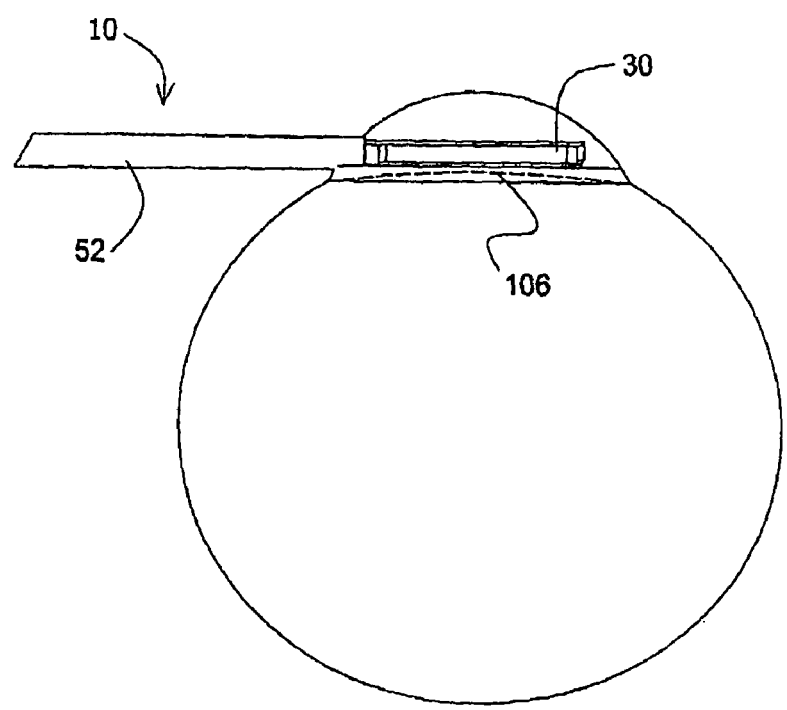

Referring to FIG. 10, after the eye is entered, the surgeon uses foot-pedal control switch 90 to advance outer tube 18, inner tube 20 (disposed inside of outer tube 18), and burning element 30, to extend and protrude from the end of sleeve 52 (FIG. 3b).

Figure 11:
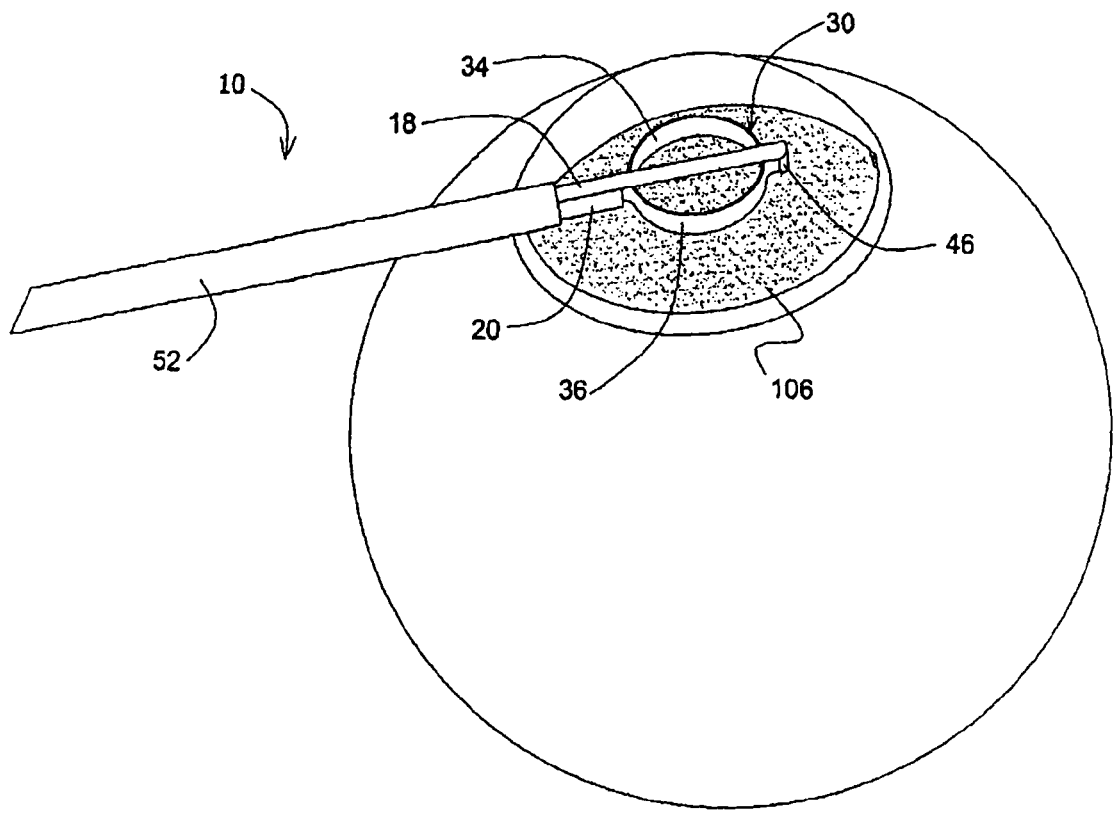
FIG. 11 illustrates the fully expanded circular burning element of the invention positioned upon the lens, moments before searing of the lens for completion of a capsulotomy.

Referring to FIG. 11, burning element 30 has been exposed, and inner tube 20 is advanced via foot-pedal control switch 90 such that bands 34, 36 of burning element 30 are pushed towards tip 46 of outer tube 18 while outer tube 18 remains stationary. This causes bands 34, 36 of burning element 30 to switch from a substantially flattened configuration (shown in FIG. 10), to semi-circular configuration (shown in FIG. 11) wherein bands 34, 36 of burning element 30 substantially form a circle with one another (also shown in FIG. 6).

With burning element 30 thus extended and circular, the surgeon lowers tool 10 such that the lens capsule 106 is contacted by bands 34, 36 of burning element 30.

A low-voltage electrical pulse is then applied using foot-pedal control switch 90, and bands 34, 36 heat up such that a capsulotomy opening is burned in the lens capsule 106 where bands 34, 36 are positioned.

Figure 12:
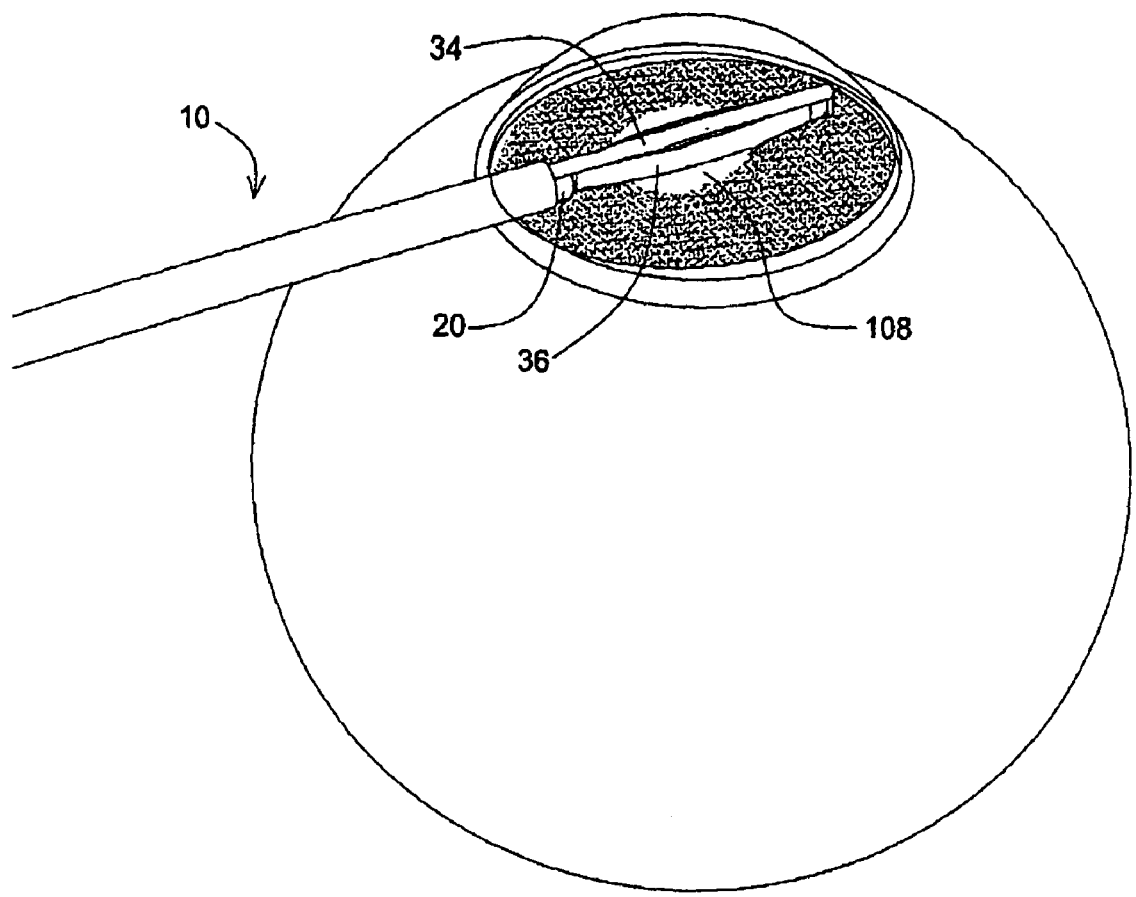
FIG. 12 illustrates the final capsulotomy, and the burning element closed and folded for removal from the lens.

Referring to FIG. 12, bands 34, 36 are then returned to the retracted configuration via backwards movement of inner tube 20. The capsulotomy opening 108 seared using the invention is apparent in the center of FIG. 12. Closing of bands 34, 36 causes any excess capsular and cortical lens material seared from the area of the capsulotomy 108 to be retained within bands 34, 36, allowing removal of this excess material.

Figure 13:
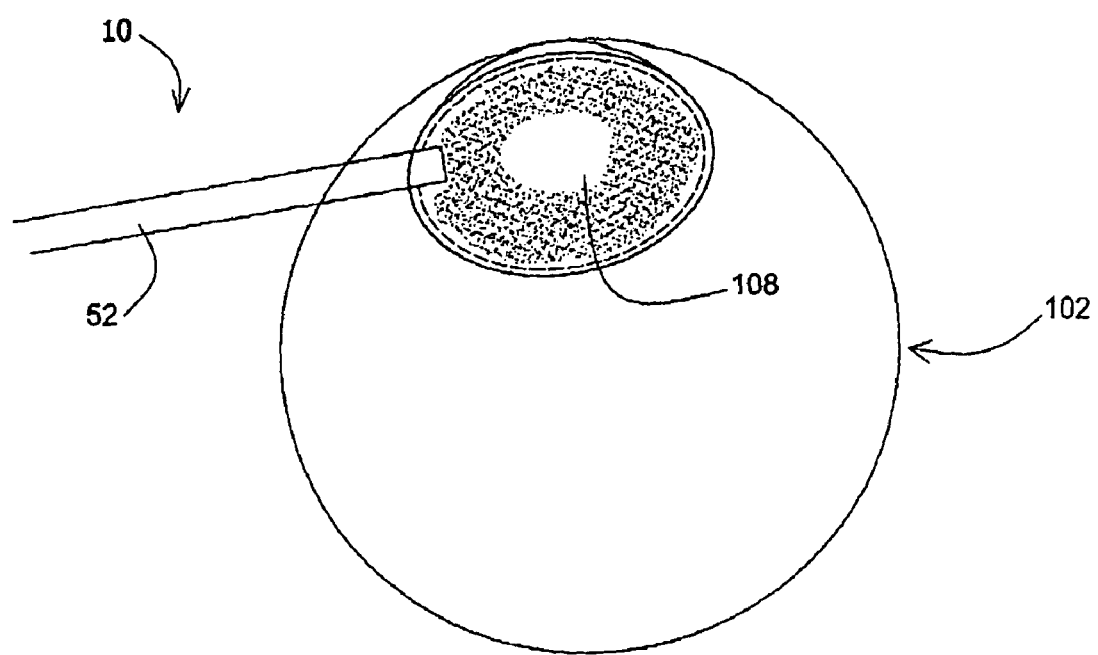
FIG. 13 illustrates the fully retracted tool being removed from the eye, and the final capsulotomy formed.

Referring to FIG. 13, all internal elements of the tool 10, including burning ring 30 and inner and outer tubes 20, 18, have been retracted to within the sleeve 52, in preparation for removal of the tool 10 from the eye 102. Apparent at the center of FIG. 13 is the final capsulotomy opening 108 formed using the capsulotomy tool and system of the invention. The tool 10 is then removed from the eye 102, and the remainder of the cataract surgery can be performed via the capsulotomy opening 108 seared.

Figure 14:
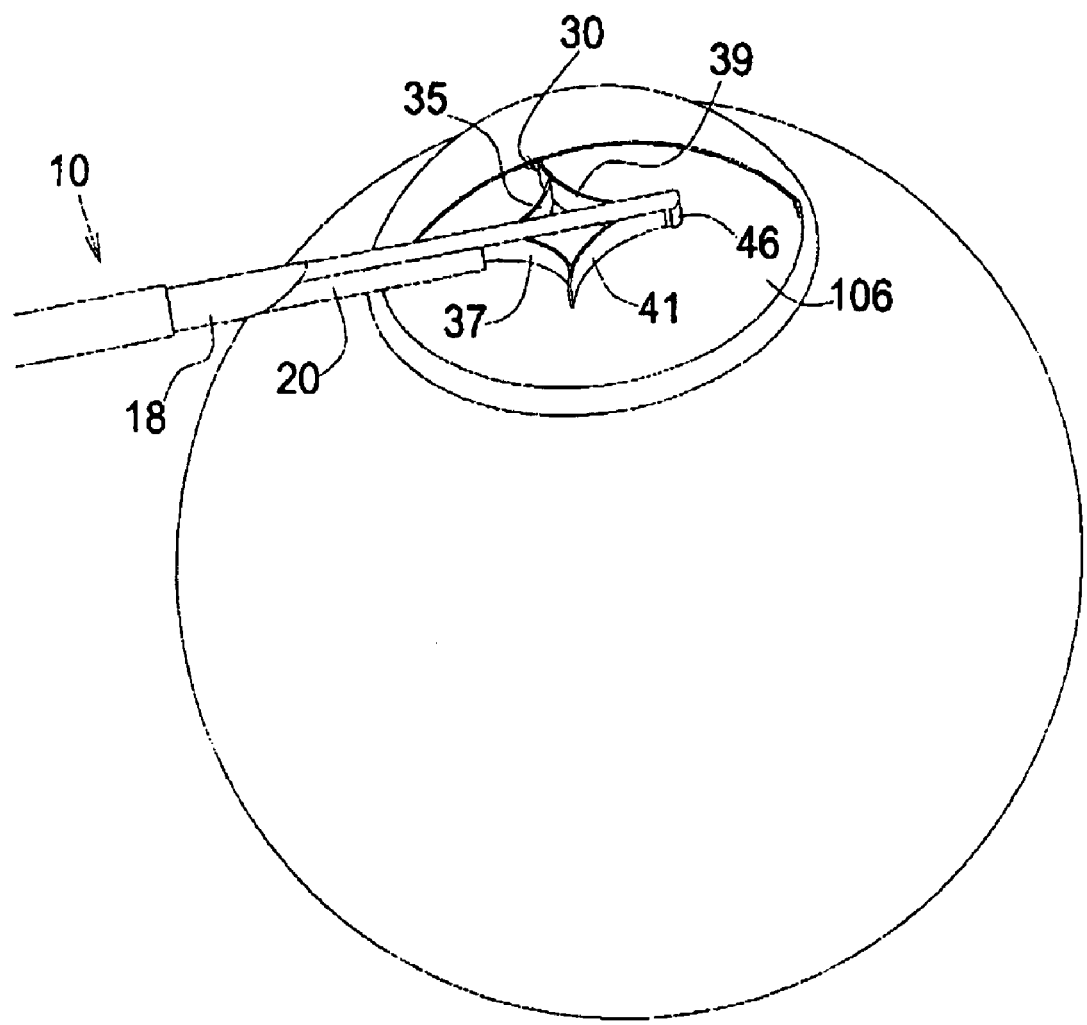
FIG. 14 illustrates the problematic scenario in which random breakage of the burning tool bands occurred while the tool was within the eye.
Figure 15:
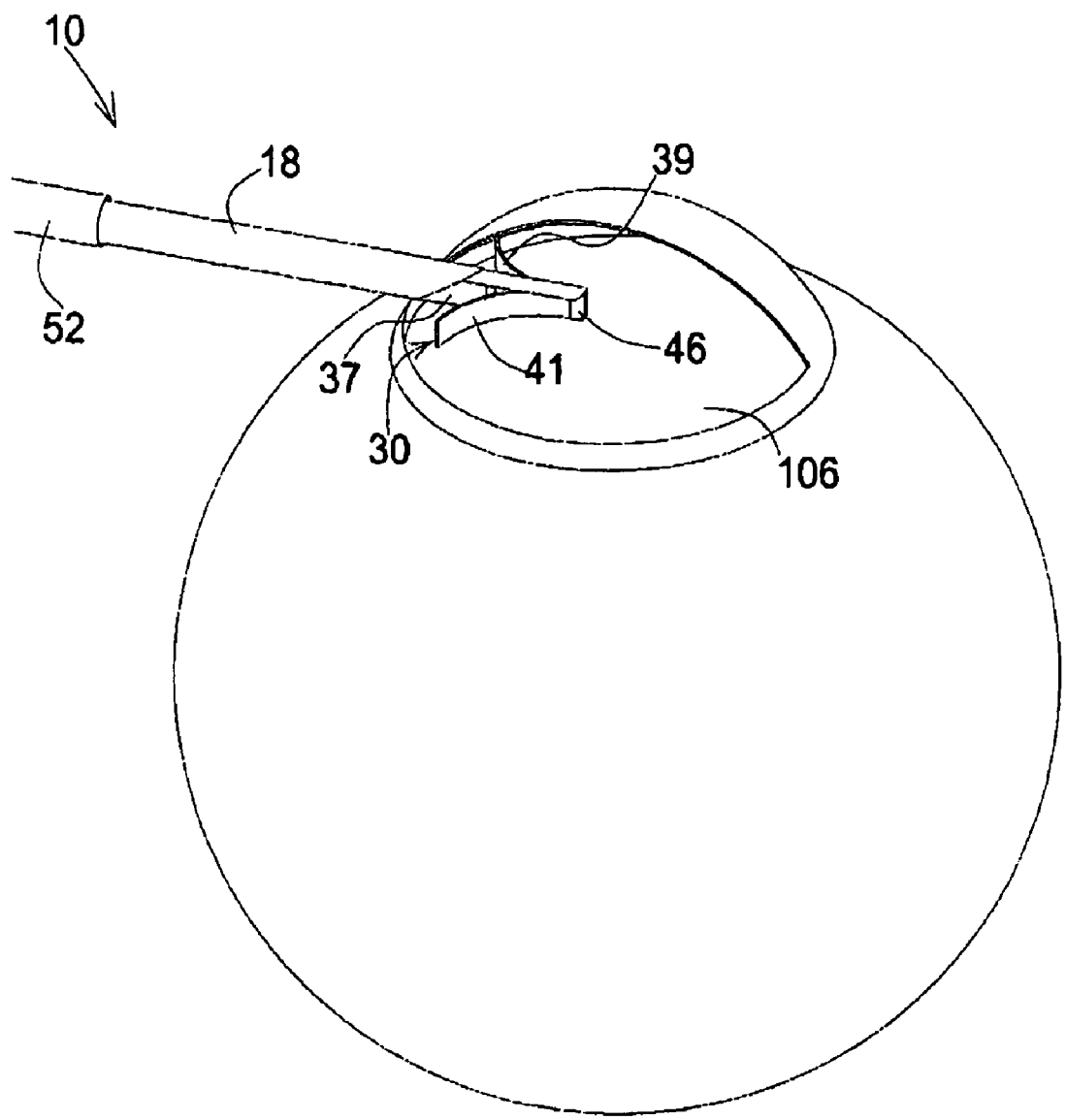
FIG. 15 further illustrates the problematic scenario of FIG. 14, showing that the upper segments of the broken band cannot be retracted into the sleeve.

FIGS. 14 and 15 describe a predicament that may occur, in which the electrical current has surged above the desirable range of voltage, and one or both of the bands have broken in a manner that prevents removal of the tool from the eye. Recall that the tool is inserted through a small opening of 1-2 millimeters, and then the burning ring is opened to a larger, circular configuration. Should the burning ring then break in the larger configuration, it is difficult to effect its removal from the eye. The solution to this problem is described in FIGS. 16-18, herein below.

Referring to FIG. 14, the bands of burning element 30 are shown after random breakage has occurred at the center of each band, due to an electrical surge. This breakage has lead to two pairs of band segments: band segments 35, 37 which remain connected to the end of inner tube 20, and band segments 39, 41 which remain connected to tip 46 of outer tube 18. Band segments (35, 39, 37, 41) remain in loose contact with one another, giving the appearance in FIG. 14 of being intact. However, the tips of the diamond-shape formed, at the center of the bands, represent severed bands. When attempts are made to retract the broken bands of the burning element, by effecting pulling of inner tube 20 to within outer tube 18 and within sleeve 52, band segments 35, 37 may move towards the midline of the tool and can be retracted. However, band segments 39, 41 remain open and cannot be retracted, as is more readily apparent in FIG. 15.

Referring to FIG. 15, segments 35, 37 have easily been retracted into sleeve 52 in the same manner as bands 34, 36 were designed to retract. However, segments 39, 41, form an arrowhead which extends beyond the size of the incision in the eye, and cannot be retracted into sleeve 52 or be removed from the eye in the extended configuration.

Figure 16:
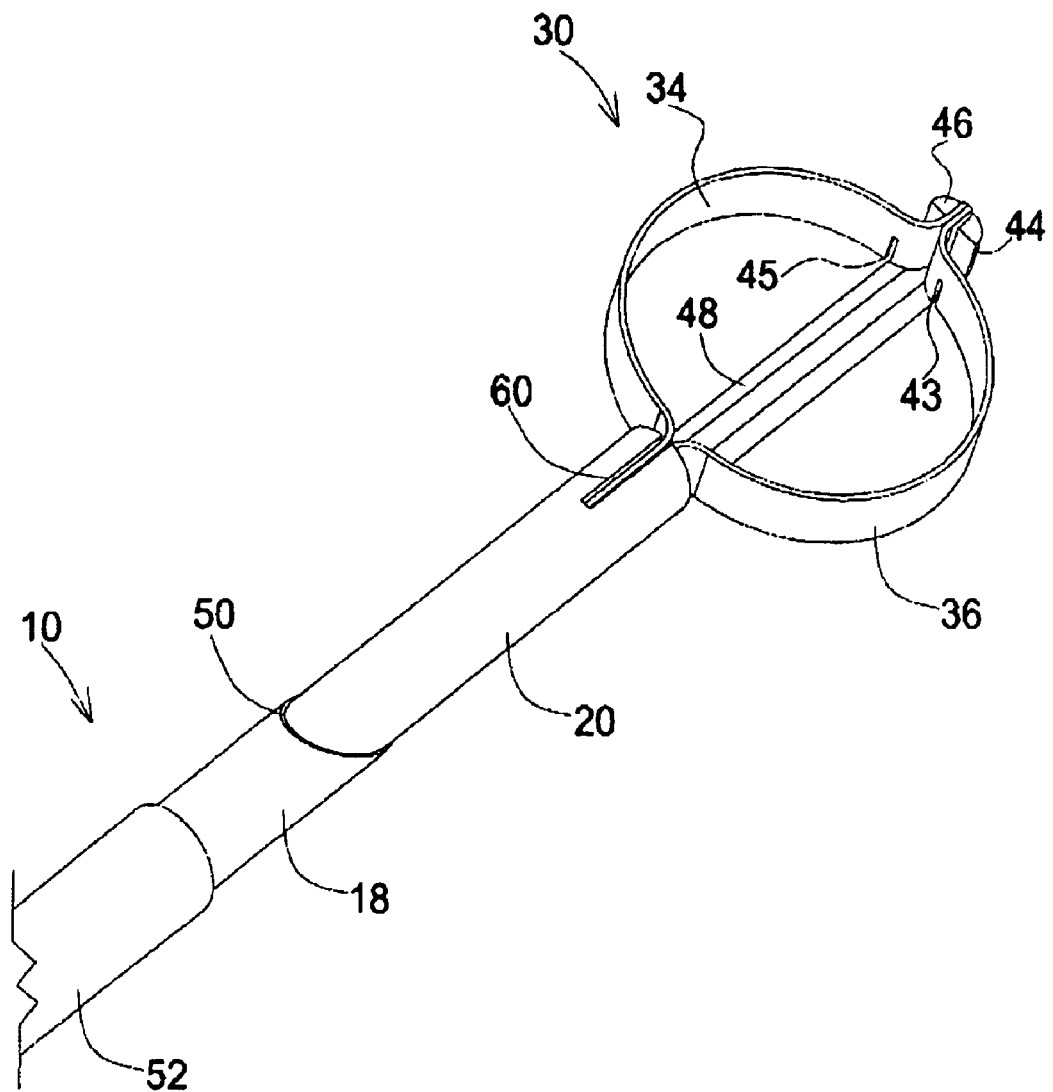
FIG. 16 is a partial view of a capsulotomy tool, showing the burning element in an extended configuration, with each band having a groove defining a predetermined point of weakness.

In order to obviate this situation, predefined points of weakness have been designed on the bands of the burning element. Referring to FIG. 16, each band 34, 36 of burning element 30 has a groove 45, 43, respectively, close to tip 46. When the electrical current is excessive, breakage will occur at the grooves 45, 43, since at these predefined weakness points the decrease in material mass leads to increased resistance to the electrical current, resulting in melting of the metal at grooves 45, 43.

Figure 17:
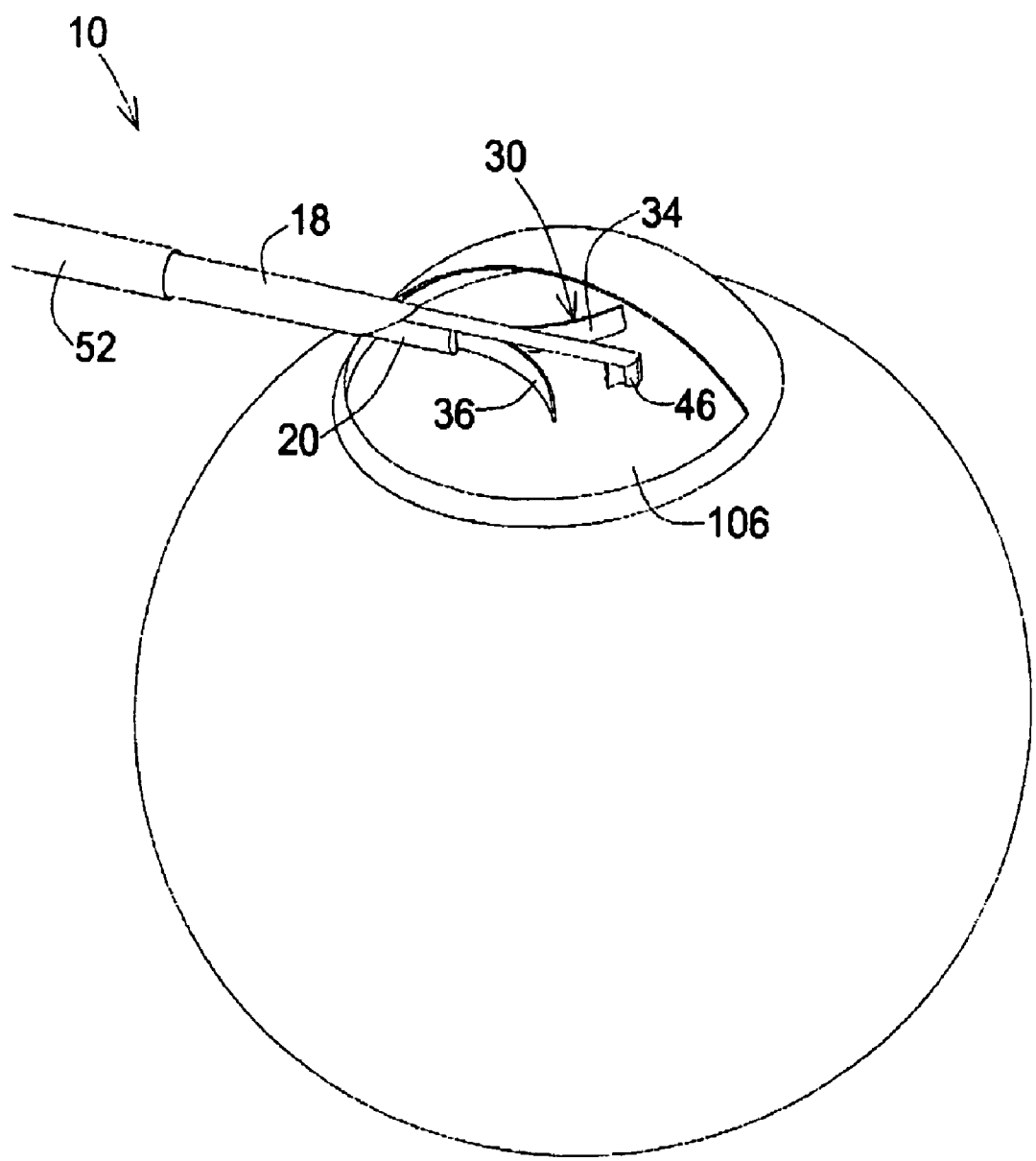
FIG. 17 illustrates the structure of the bands after breaking at predetermined weakness points, while the tool is still in the eye.

Referring to FIG. 17, bands 34, 36 of burning element 30 are shown after breakage has occurred at the predefined points of weakness (i.e., at grooves 43, 45 at the distal end of the bands). Thus, in this case, as can be seen, bands remain connected to inner tube 20 at the proximal end of the burning element. The overturned arrowhead-shape formed by broken bands 34, 36, allows simple retraction of broken bands back into sleeve 52, in preparation for removal of tool 10 from eye 102. Broken bands 34, 36 can be moved toward the midline of the tool, parallel to the horizon, and after retraction into the outer tube 18 and the sleeve, broken bands 34, 36 will not protrude beyond the minimal-sized incision made in the eye.

Figure 18:
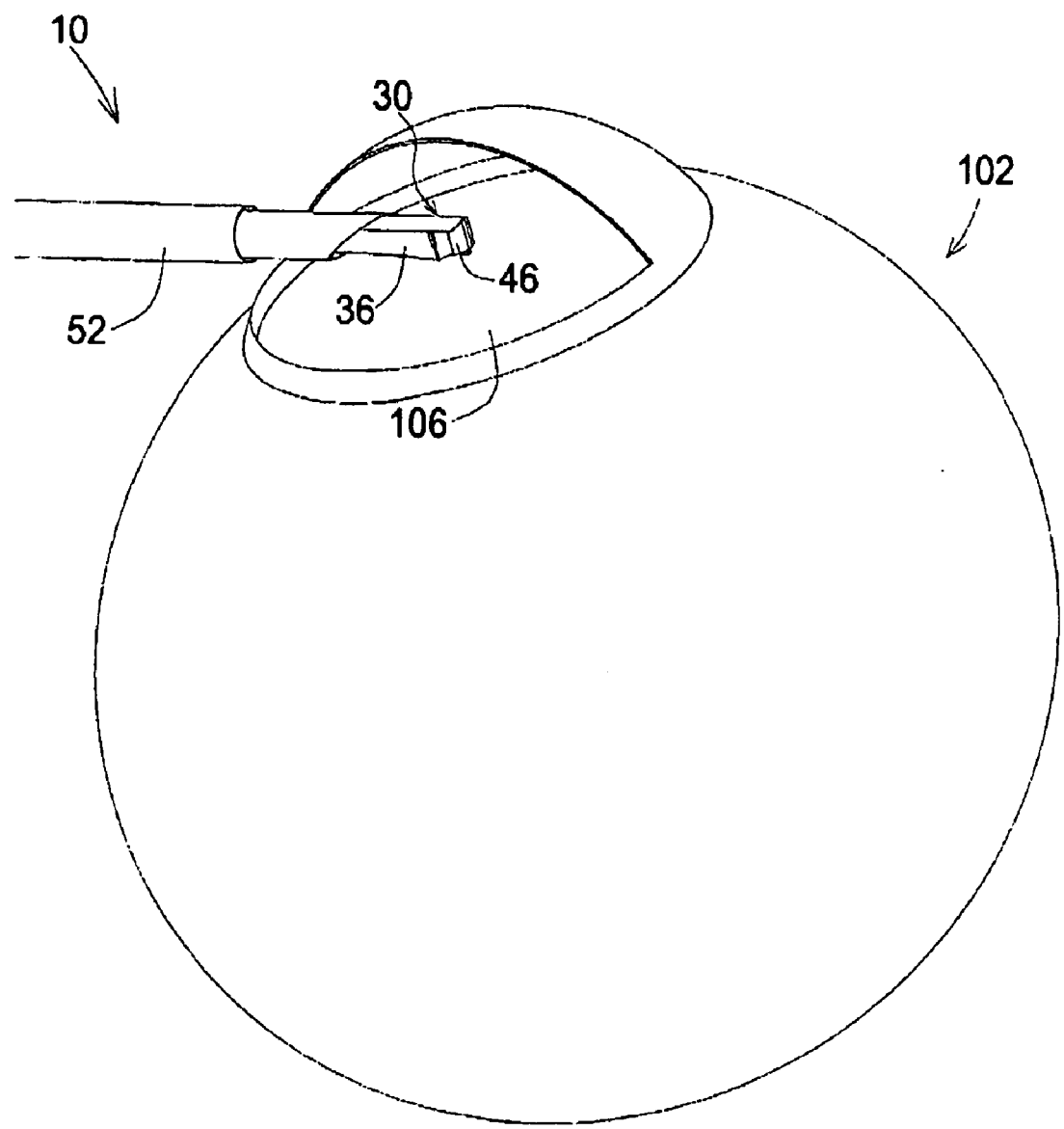
FIG. 18 illustrates the fully retracted tool being removed from the eye.

Referring to FIG. 18, all internal elements of tool 10, including broken bands 34, 36 have been retracted to within the sleeve 52, in preparation for removal of tool 10 from eye 102. Tool 10 may now be removed from eye 102.

Thus, the improved design shown in FIGS. 16-18, having predefined points of weakness, preferably present near the distal tip 46, allows for easy removal of the tool after undesirable breakage has occurred in the bands of the burning element.

The system and tool provide an effective and reproducible capsular opening in the lens and allows further steps of cataract surgery, such as phacoemulsification or an equivalent procedure, and removal of cataract material.

Thus, the tool of the present invention provides a very significant advantage when compared with capsulotomy tools of the prior art. The extendable-retractable burning element allows for performance of a capsulotomy in a quick and efficient manner, leaving a capsular opening that is clean and tear resistant. Moreover, the extendable-retractable burning element allows for entry into the eye via a corneal incision on the order of 1-2 millimeters, while allowing for a large capsulotomy, for example, 5-7 millimeters. Using the capsulotomy tool of the present invention, the surgical procedure is simplified, since the surgeon does not need to use a separate device for providing pressurized air to the surgical site.

Using the present invention, a complete circle or a complete oval-shaped searing takes place, so that there is no need for tearing of the lens using forceps, which would be difficult to perform and to control.

Having described the invention with regard to certain specific embodiments thereof, it is to be understood that the description is not meant as a limitation, as further modifications will now become apparent to those skilled in the art, and it is intended to cover such modifications as fall within the scope of the appended claims.

The invention claimed is:

1. A tool for performing a capsulotomy, comprising;
   (a) a main housing having a proximal end and a distal end;
   (b) an inner tube extending longitudinally through said main housing and extending from the distal end of said main housing;
   (c) an outer tube that extends longitudinally through said main housing and extends from said distal end of said main housing, wherein said inner tube is disposed inside of said outer tube, and wherein said inner tube is movable with respect to said outer tube
   (d) an extendable-retractable burning element, comprising first and second electrically conductive bands, said bands having opposite ends that are connected between the end of said inner tube and the tip of said outer tube, said burning element being adapted for switching between a retracted configuration and an extended configuration, by said movement of said inner tube with respect to said outer tube;
   (e) a groove present on each of said first and second bands, said grooves providing predefined points of weakness allowing for controlled breakage of said burning element at said grooves, during an event of excessive electrical current;
   (f) an airflow channel extending through said main housing and terminating proximal to said burning element;
   (g) airflow means coupled to the airflow channel for supplying pressurized airflow; and
   (h) capsulotomy and movement control means coupled to the main housing for providing electrical current to the burning element and movement control for controlling extending and retracting of the burning element,
wherein said retractable burning element is insertable into the eye through a small corneal incision when said burning element is in a retracted configuration, and said burning element is adapted to perform of a capsulotomy of a predetermined size when it is in an extended configuration and an electrical current is applied to said burning element.

2. The tool of claim 1, wherein the outer tube is electrically insulated from the inner tube, and wherein each one of said outer tube and said inner tube defines an opposite pole of an electrical circuit.

3. The tool of claim 1, wherein said outer tube comprises a circumferentially truncated extension at the end region thereof, and wherein said outer tube further comprises a tip at which location said truncated extension ends.

4. The tool of claim 3, wherein the outer tube has a beveled edge located at the interface between said truncated extension and the remainder of said outer tube.

5. The tool of claim 1, wherein in said retracted configuration, said bands are positioned substantially parallel to one another and above said truncated extension and wherein in said maximally extended configuration, said bands are concavely arched so as to form a substantial circle with one another.

6. The tool of claim 5, wherein in the extended configuration, said bands form a complete circle having a diameter of approximately 4-7 millimeters.

7. The tool of claim 1, wherein said first and second bands are formed from a tungsten alloy.

8. The tool of claim 1, wherein movement of said inner tube towards said tip of said outer tube causes said burning element to switch from said retracted configuration to said extended configuration.

9. The tool of claim 1, further comprising a sleeve disposed over said outer tube, said sleeve being formed from a non-conductive material.

10. The tool of claim 9, wherein said sleeve is formed from plastic or Teflon, having smooth sides such that entry into the eye can be achieved with minimal friction.

11. The tool of claim 1, wherein said burning element is removable prior to use, and can be selected from a variety of sized burning elements in order to choose the capsulotomy size.

12. The tool of claim 1, wherein said burning element is capable of searing a capsulotomy having a diameter selected from one of the following diameters:
   4 mm, 5 mm, 6 mm and 7 mm.

13. The tool of claim 1, wherein said airflow channel is located inside of said inner tube.

14. The tool of claim 1, wherein said burning element is capable of searing a complete capsulotomy of a substantially circular or oval shape, without the need for forceps manipulation or tearing of the capsulotomy.

15. The tool of claim 1, wherein said tool is disposable, and is designed for a single use.

16. The tool of claim 1, wherein each of said grooves is located adjacent to the distal end of said tool, allowing for retraction of said bands in the event of band breakage.

17. The tool of claim 1, wherein each of said grooves is located adjacent to the tip of said outer tube.

18. A system for performing a capsulotomy procedure, comprising;
   (a) the capsulotomy tool of claim 1; and
   (b) a capsulotomy and movement control unit;
wherein said tool is in connection with said capsulotomy and movement control unit for providing electrical current and movement control to said burning element such that when said burning element is extended and heated, an opening is burned on the lens capsule.

19. The system of claim 18, further comprising a handle connecting between said tool and said capsulotomy and movement control unit.

20. The system of claim 18, further comprising an air pressure unit and airflow means coupled to the air pressure unit for directing pressurized air to the surgical site.

* * * * *